United States Patent [19]

Leone et al.

[11] Patent Number: 5,728,068
[45] Date of Patent: Mar. 17, 1998

[54] MULTI-PURPOSE BALLOON CATHETER

[75] Inventors: James Ernest Leone; Karl Phillip Weissinger; Margaret Frances Yoklavich, all of Miami, Fla.

[73] Assignee: Cordis Corporation, Miami Lakes, Fla.

[21] Appl. No.: 580,161

[22] Filed: Dec. 28, 1995

Related U.S. Application Data

[63] Continuation-in-part of Ser. No. 259,534, Jun. 14, 1994, Pat. No. 5,505,700.
[51] Int. Cl.$^6$ ............................................. A61M 29/00
[52] U.S. Cl. ........................... 604/101; 604/102; 604/104; 606/108
[58] Field of Search ............................. 604/20, 21, 52, 604/53, 96–104, 107, 113, 114, 246; 606/191–197, 108; 607/115, 116, 120, 121, 122, 124; 128/656, 658

[56] References Cited

U.S. PATENT DOCUMENTS

| | | | |
|---|---|---|---|
| 4,423,725 | 1/1984 | Baran et al. | 604/101 |
| 4,546,759 | 10/1985 | Solar . | |
| 4,640,298 | 2/1987 | Pless et al. | 607/124 |
| 4,681,564 | 7/1987 | Landreneau . | |
| 4,776,349 | 10/1988 | Nashef et al. | 607/122 |
| 4,824,436 | 4/1989 | Wolinsky | 604/53 |
| 4,968,307 | 11/1990 | Dake et al. . | |
| 5,019,075 | 5/1991 | Spears et al. | 606/194 |
| 5,021,044 | 6/1991 | Sharkawy . | |
| 5,056,532 | 10/1991 | Hull et al. | 607/124 |
| 5,087,243 | 2/1992 | Avitall . | |
| 5,169,395 | 12/1992 | Narciso, Jr. . | |
| 5,236,413 | 8/1993 | Feiring | 604/21 |
| 5,279,546 | 1/1994 | Mische et al. . | |
| 5,286,254 | 2/1994 | Shapland et al. | 604/21 |
| 5,298,018 | 3/1994 | Narciso, Jr. . | |
| 5,315,992 | 5/1994 | Dalton . | |
| 5,360,440 | 11/1994 | Andersen | 607/116 |
| 5,368,034 | 11/1994 | Isner . | |
| 5,370,608 | 12/1994 | Sahota et al. | 604/20 |
| 5,380,299 | 1/1995 | Fearnot et al. . | |
| 5,383,928 | 1/1995 | Scott et al. . | |
| 5,405,322 | 4/1995 | Lennox et al. | 604/53 |
| 5,423,744 | 6/1995 | Gencheff et al. | 604/21 |
| 5,439,446 | 8/1995 | Barry | 604/96 |
| 5,484,412 | 1/1996 | Pierpont | 604/101 |
| 5,505,700 | 4/1996 | Leone et al. | 604/96 |
| 5,507,724 | 4/1996 | Hofmann et al. | 604/53 |
| 5,514,092 | 5/1996 | Forman et al. | 604/101 |

FOREIGN PATENT DOCUMENTS 9505866  3/1995  WIPO .

*Primary Examiner*—Corrine M. McDermott
*Assistant Examiner*—Cris L. Rodriguez
*Attorney, Agent, or Firm*—Michael W. Montgomery

[57] ABSTRACT

The multi-purpose balloon catheter comprises a tubular body having a proximal end portion, a distal end portion and at least two lumens within the tubular body. The distal end portion has three spaced apart balloons thereon, the distal balloon being an occlusive balloon, the middle balloon being a stent mounting balloon and the proximal balloon being an occlusive balloon.

21 Claims, 3 Drawing Sheets

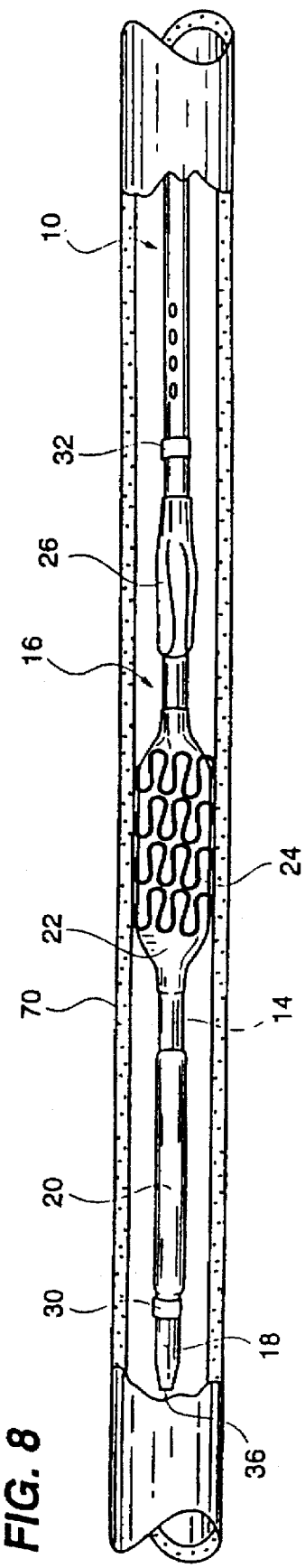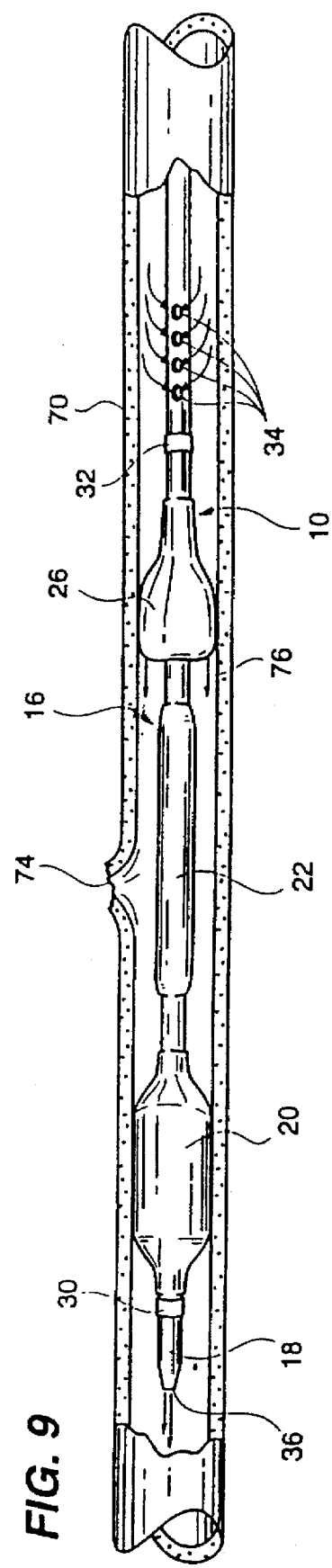
FIG. 8
FIG. 9

MULTI-PURPOSE BALLOON CATHETER

This is a continuation-in-part of patent application Ser. No. 08/259,534, filed on Jun. 14, 1994, now U.S. Pat. No. 5,505,700.

BACKGROUND OF THE INVENTION

1. Field of the Invention

The present invention relates to a multi-purpose balloon catheter having an angioplasty, occlusive/drug delivery or photodynamic therapy (PDT) balloon, a stent delivery balloon or iontophoresis section, and a drug delivery occlusive balloon in a distal end portion of the catheter. For this purpose, the multi-purpose balloon catheter of the present invention includes two or more lumens therein extending to the distal end portion of the multi-purpose balloon catheter.

2. Description of the Related Art Including Information Disclosed Under 37 CFR §§1.97–1.99.

Heretofore numerous balloon type catheters and perfusion catheters have been proposed for performing one or two procedures. However, heretofore, prior to the present invention a multi-purpose balloon catheter capable of performing three or more cardiovascular procedures has not been available.

Three non-analogous three balloon catheters are disclosed in the Solar U.S. Pat. No. 4,546,759, the Landreneau U.S. Pat. No. 4,681,564 and the Dalton U.S. Pat. No. 5,315,992.

A simultaneous angioplasty and drug delivery balloon is disclosed in PCT published patent application No. 9,505,866.

Examples of catheters for delivering thrombolytic agents to a blood vessel are disclosed in the following U.S. Patents.

| U.S. Pat. No. | Patentee |
| --- | --- |
| 4,968,307 | Dake et al. |
| 5,021,044 | Sharkawy |
| 5,279,546 | Mische et al. |
| 5,368,034 | Isner |
| 5,380,299 | Fearnot et al. |

Two methods for photodynamic therapy (PDT) treatment of blood vessels including use of a balloon are disclosed in the Narciso, Jr. U.S. Pat. Nos. 5,169,395 and 5,298,018.

Finally, an implantable system for myocardial iontophoretic delivery of medicinal materials to a heart is disclosed in U.S. Pat. No. 5,087,243, a drug delivery apparatus including a balloon catheter is disclosed in U.S. Pat. No. 5,286,254; an apparatus for inducing permeation of medication into internal tissue and including a balloon catheter and an internal electrode is disclosed in U.S. Pat. No. 5,236,413; and, a catheter system for the deployment of biological material is disclosed in U.S. Pat. No. 5,423,744.

SUMMARY OF THE INVENTION

According to the present invention there is provided a multi-purpose balloon catheter comprising a tubular body having a proximal end portion, a distal end portion and at least two, and preferably four, lumens within the tubular body, and the distal end portion having three spaced apart balloons thereon, the distal balloon being an occlusive balloon, the middle balloon being a stent mounting balloon and the proximal balloon being an occlusive balloon.

Preferably the distal balloon is an angioplasty balloon and the proximal balloon is also a drug therapy balloon.

BRIEF DESCRIPTION OF THE DRAWINGS

FIG. 8 is a longitudinal view of the blood vessel shown in FIG. 6 with portions cut away and shows the distal end portion of the multi-purpose balloon catheter of the present invention disposed therein but with the angioplasty balloon and the thrombolysis balloon collapsed and with a stent mounting (delivery) balloon disposed between them inflated for the purpose of stent implantation.

FIG. 9 is a longitudinal view of the blood vessel shown in FIG. 6 with portions cut away and shows the distal end portion of the multi-purpose balloon catheter of the present invention disposed therein, similar to the view shown in FIG. 6, but shows an aneurysm in the portion of the blood vessel between the first, angioplasty balloon and the third occlusive/drug delivery balloon.

DESCRIPTION OF THE PREFERRED EMBODIMENT(S)

Figure 1:
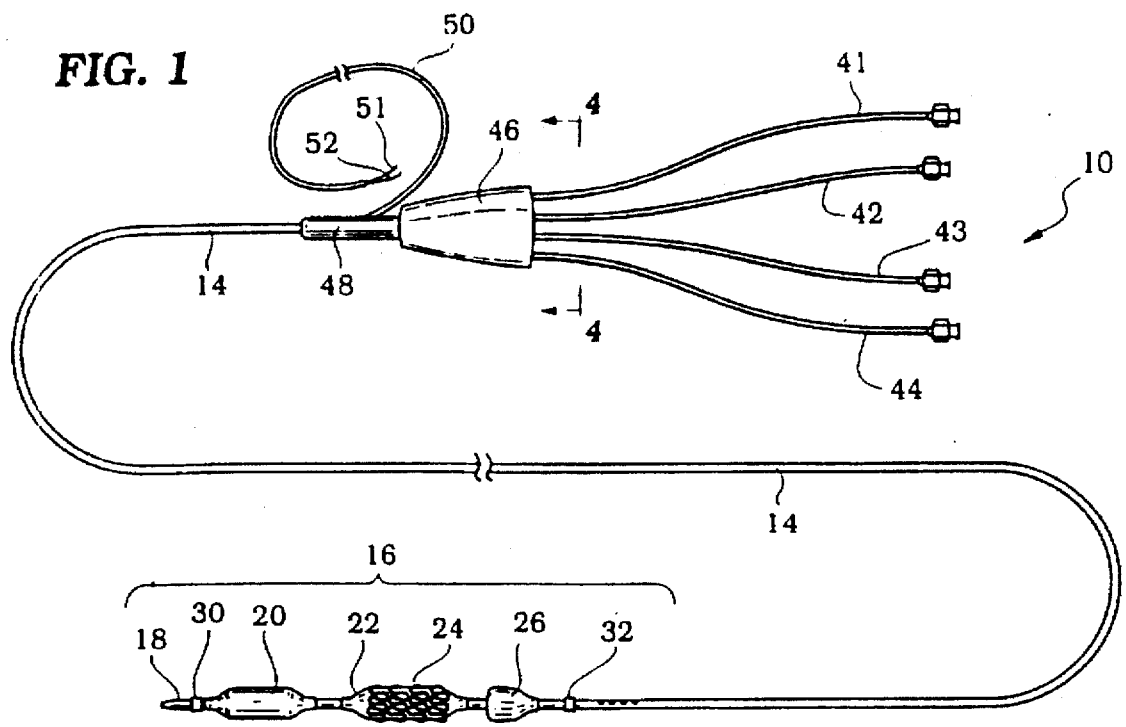
FIG. 1 is a plan view of the multi-purpose balloon catheter constructed according to the teachings of the present invention and shows a distal end portion of the catheter and a proximal end portion of the catheter.

Referring now to the drawings in greater detail, there is illustrated in FIG. 1 a multi-purpose balloon catheter 10 constructed according to the teachings of the invention and including a proximal end portion 12, a tubular body 14, and a distal end portion 16 including a distal tip 18. According to the teachings of the present invention, the distal end portion 16 includes a first, most distal, occlusive/angioplasty/photodynamic balloon 20, a second, or middle stent mounting or stent delivery balloon 22 capable of carrying a stent 24 thereon, which can be a metal stent or a thermoplastic stent, and a third, occlusive/drug delivery balloon 26.

As shown, the tip 18 has a distal ring electrode 30 which is electrically coupled with a distal ring electrode 32 located just proximally of the occlusive balloon 26.

Proximal of the ring electrode 32 are one or more, namely four, perfusion ports 34. Typically, the distal tip 18 is open at the outer end thereof to form a perfusion port 36 which is in communication with a perfusion lumen 38 within the tubular body 14 in the distal end portion 16 which is also in communication with the perfusion ports 34.

The proximal end portion 12 includes four input tubings 41–44 connected to a coupling member 46 that couples through a strain relief sleeve 48 to the tubular body 14. Also coupled to the strain relief sleeve 48 is an electrical cable 50 having at least two insulated wire conductors 51 and 52 that extend through the tubular body to the electrodes 30, 32 and the stent 24. Wire conductor 51 connects to the ring electrodes 30 and 32 and wire conductor 52 connects to the stent 24.

Figure 2:
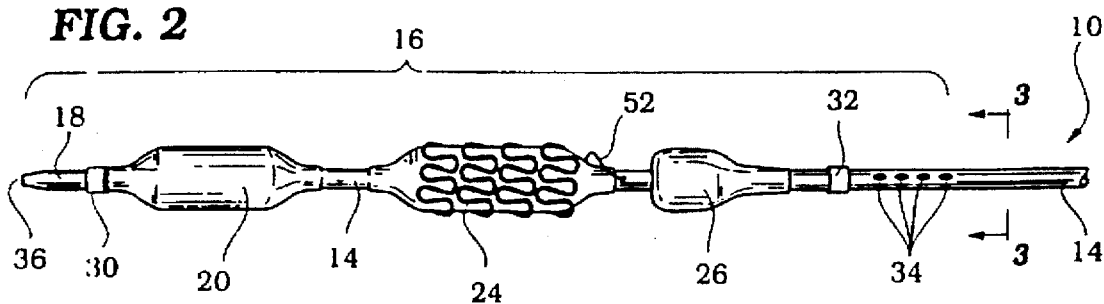
FIG. 2 is an enlarged view of the distal end portion of the catheter shown in FIG. 1 and shows a first angioplasty balloon, a second or middle stent mounting balloon and a third, occlusive/drug delivery balloon.
Figure 3:
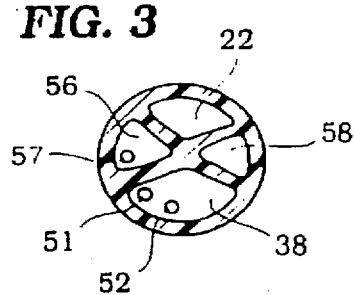
FIG. 3 is a sectional view taken along lines 3—3 of FIG. 2.

FIG. 3 is a sectional view through the tubular body 14, is taken along line 3—3 of FIG. 2 and shows the perfusion lumen 38, which is the largest lumen, a fluid delivery lumen 54 for the stent mounting balloon 22 directly above the perfusion lumen 38, a fluid delivery lumen 56 for the angioplasty balloon 20 which also can have an light delivery fiber 57 therein, and a fluid delivery lumen 58 for delivering a fluid and/or drug to the occlusive/drug delivery balloon 26.

Figure 4:
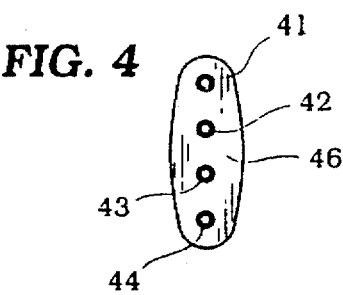
FIG. 4 is a sectional view taken along lines 4—4 of FIG. 1.

FIG. 4 is a sectional view of the tubings 41–44 shown in FIG. 1 and is taken along line 4—4 of FIG. 1.

The multi-purpose balloon catheter 10 of the present invention can be utilized for performing a number of procedures which will now be described in greater detail in connection with the description of FIGS. 5–9.

Figure 5:
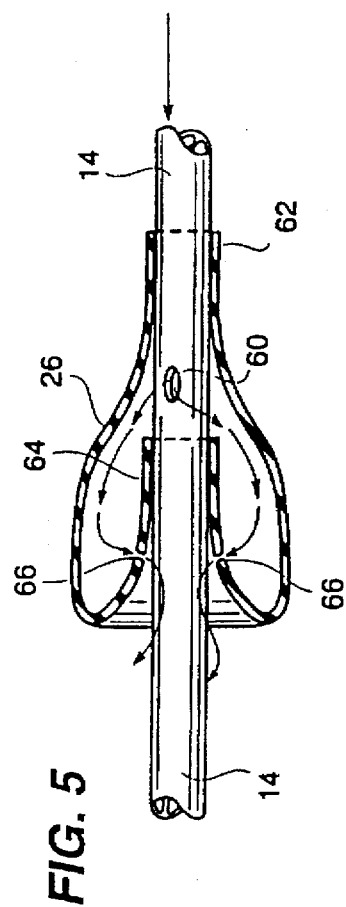
FIG. 5 is an enlarged cross-sectional view of the occlusive/drug delivery balloon shown in FIG. 2.

First of all, as shown in FIG. 5, the occlusive/drug balloon 26 has a proximal end 60 fixed on the tubular body just proximal to a fluid delivery inlet port 62. The balloon 26 has a distal end portion 64 which is inverted, or folded under itself, over the tubular body 14 and connected thereto as shown. Then, two or more outlet ports 66 are provided in an inwardly facing section 67 of the distal end portion 64 of the balloon 26.

Figure 7:
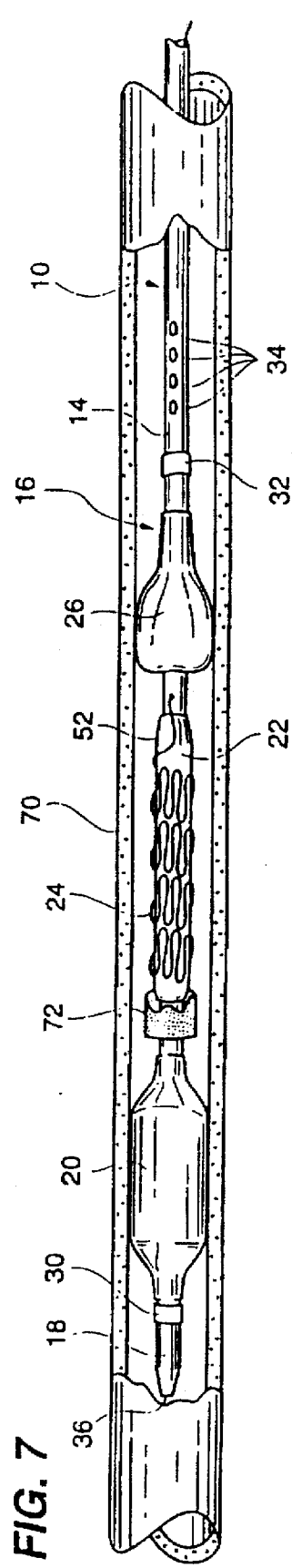
FIG. 7 is a longitudinal view of the blood vessel shown in FIG. 6 with portions cut away and shows the distal end portion of the multi-purpose balloon catheter therein, similar to the view shown in FIG. 5, but with a proximally located third, occlusive/drug delivery balloon also inflated.

The balloon construction for the third balloon 26 illustrated in FIG. 5 is preferred when the third balloon 26 is used for drug delivery and can be used with a saline solution for other procedures illustrated in FIGS. 7 and 9. However, for these procedures it is desirable to use a balloon not having the outlet ports 66.

Figure 6:
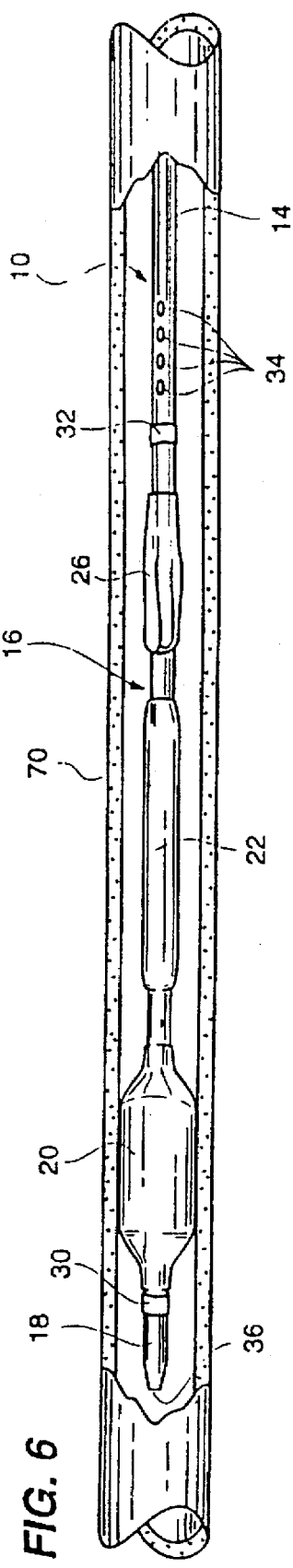
FIG. 6 is a longitudinal view with portions cut away of a section of a blood vessel and shows the distal end portion of the multi-purpose balloon catheter of the present invention disposed therein and with the first, most distal, balloon thereof in an inflated condition.

In FIG. 6, there is illustrated the distal end portion 16 of the multi-purpose balloon catheter 10 positioned in a blood vessel 70 and having the angioplasty balloon 20 inflated for an angioplasty procedure. If desired, the angioplasty balloon 20 can be made of a transparent or translucent plastic material and light can be supplied through the light delivery fiber 57 and directed through the transparent or translucent balloon 20 for photodynamic therapy.

In FIG. 7, there is illustrated an iontophoresis procedure which can include drug delivery or thrombolysis. In this procedure, the first balloon 20 is only inflated sufficient to occlude the blood vessel 70 and the third, occlusive balloon 26 is supplied with a drug solution from the lumen 58 and the inlet port 62 which is used for both inflating the balloon 26 from the lumen 58 through the inlet port 62 and for delivering a drug solution through the outlet port 66 of the balloon 26 to the area in the blood vessel 70 between the first balloon 20 and the third balloon 26.

If desired, the stent 24 can be used as an electrode and for this purpose covered with a porous polycarbonate membrane 72, a fragmentary portion of which is shown in FIG. 7. This covering will prevent shorting of the stent electrode 24 to the inner wall of the blood vessel 70.

The iontophoresis electrical circuit is completed through a silver oxide (+) or silver (−) electrodes 30, 32 depending on the polarity needed.

Also, the first balloon 20 can be an inversion of the drug delivery balloon 26 and can be constructed in the same manner but as a mirror image of the balloon 26 shown in FIG. 5 whereby drug delivery is supplied through both the first and third balloons 20 and 26 which serve as occlusive and drug delivery balloons for this procedure.

In FIG. 8 there is illustrated a stent implantation procedure where only the middle, second, stent delivery balloon 22 is inflated for implanting the stent 24. If desired, the stent 24 can be a drug delivery stent of the type disclosed in U.S. patent application Ser. No. 08/304,163 filed on Sep. 12, 1994 and entitled: RETRIEVABLE DRUG DELIVERY STENT, the disclosure of which is incorporated herein by reference. Also, a polymer, non-degradable or bio-degradable drug carrying stent sheath for encompassing at least a portion of a stent for local drug delivery is disclosed in U.S. Pat. No. 5,383,928.

Thus, in the procedure shown in FIG. 8, the stent 24 can be implanted and, if desired, utilized for delivery of a drug through the stent to the inner wall of the blood vessel 70.

In FIG. 9, there is illustrated the use of the multi-purpose balloon catheter 10 as a "bail-out catheter" where the first and third balloons are positioned on either side of an aneurysm or thrombosis and inflated to bridge the aneurysm. In this use of the multi-purpose balloon catheter 10, the third balloon 26 can be used to deliver a lysing agent 76 or other substance through the outlet ports 66 to the area of the aneurysm.

At the same time, blood can flow through the perfusion ports 34, then through the perfusion lumen 38 and out the perfusion outlet port 36 to maintain blood flow while the aneurysm 74 is being treated.

From the foregoing description, it will be apparent that the multi-purpose balloon catheter of the present invention has a number of advantages, some of which have been described above and others which are inherent in the invention.

Also, it will be apparent that modifications can be made to the multi-purpose balloon catheter of the present invention without departing from the teachings of the invention. For example, a stent 24 can be omitted from the second balloon 22 when performing the procedures shown in FIGS. 6 and 9. Also, the balloon 26 can be constructed without outlet ports 66. Further, the first balloon 20 can have a mirror image construction of the balloon 26 (inverted from the construction shown in FIG. 5).

Accordingly, the scope of the invention is only to be limited as necessitated by the accompanying claims.

We claim:

1. A multi-purpose balloon catheter comprising a tubular body having a proximal end portion, a distal end portion, and at least two lumens within said tubular body, said distal end portion having three spaced apart balloons thereon, said balloons being positioned proximal, middle, and distal relative to each other, the distal balloon being an occlusive balloon, the middle balloon being a stent mounting balloon having a stent mounted thereon, and the proximal balloon being an occlusive balloon, one of said lumens communicating with said middle balloon, said tubular body defining at least one proximal perfusion port located proximally of said proximal balloon and at least one distal perfusion port located distally of said proximal perfusion port, the other of said lumens communicating between said proximal and distal perfusion ports.

2. The multi-purpose balloon catheter of claim 1, further comprising a third lumen defined by said tubular member that communicates with said proximal and distal balloons.

3. The multi-purpose balloon catheter of claim 1, further comprising a third and fourth lumen defined by said tubular member, the third lumen communicating with said proximal balloon and the fourth lumen communicating with said distal balloon, said distal balloon being an angioplasty balloon.

4. The multi-purpose balloon catheter of claim 1, further comprising an electrode forming stent mounted about said middle balloon and an electric wire connected to said electrode forming stent which extends through said tubular body to said proximal end portion of said tubular body.

5. The multi-purpose balloon catheter of claim 4 wherein said electrode forming stent has a microporous covering thereover to prevent shorting of said stent electrode to an interior wall of a blood vessel.

6. The multi-purpose balloon catheter of claim 4 including at least one second electrode mounted on said tubular body.

7. The multi-purpose balloon catheter of claim 6 wherein said second electrode is mounted on said tubular body proximally of said proximal balloon.

8. The multi-purpose balloon catheter of claim 6, wherein said second electrode is mounted on said tubular body distally of said distal balloon.

9. The multi-purpose balloon catheter of claim 4 wherein said proximal balloon is a drag delivery balloon having an inwardly facing surface that faces inwardly toward said tubular body and defining drug delivery outlet ports that open onto the inwardly facing surface.

10. The multi-purpose balloon catheter of claim 1 wherein said proximal balloon is also a drug delivery balloon.

11. The multi-purpose balloon catheter of claim 1 wherein said distal balloon is also an angioplasty balloon.

12. The multi-purpose balloon catheter of claim 1 wherein said distal balloon is a transparent or translucent photodynamic therapy balloon and wherein said catheter has a light delivery fiber therein extending to said photodynamic therapy balloon.

13. The multi-purpose balloon catheter of claim 1 wherein said distal balloon is a drug delivery balloon.

14. A multi-purpose balloon catheter, comprising:

a tubular catheter body having a proximal and distal end portion, said tubular body defining a first, second and third inflation lumen;

a first, second and third balloon affixed to said distal end portion of the tubular body and being longitudinally spaced from each other, said first balloon being a relatively elastic occlusive balloon positioned proximal of the second balloon, and the second balloon being a stent mounting balloon positioned proximal of the third balloon, the third balloon being a relatively inelastic angioplasty balloon;

a hub affixed to the proximal end portion of the tubular body and defining a first, second and third inflation port, wherein the first, second and third inflation lumen provide fluid communication between the first, second and third inflation port and the first, second and third balloon, respectively.

15. The multi-purpose balloon catheter of claim 14, further comprising an electrode mounted about the second balloon, and an electrically conductive wire which extends through said tubular body to said proximal end portion of said tubular body, said electrode being coupled to said wire.

16. The multi-purpose balloon catheter of claim 14, wherein said proximal balloon is a drug delivery balloon and defines at least one drag delivery outlet port.

17. A multi-purpose balloon catheter, comprising:

a tubular catheter body having a proximal and distal end portion, said tubular body defining a proximal and distal perfusion port, the tubular body further defining an inflation lumen and a perfusion lumen, the perfusion lumen providing fluid communication between the proximal and distal perfusion ports;

a first, second and third balloon affixed to said distal end portion of the tubular body and being longitudinally spaced from each other, said first balloon being an occlusive balloon positioned proximal of the second balloon, and the second balloon being a stent mounting balloon positioned proximal of the third balloon, the third balloon being an occlusive balloon;

a hub affixed to the proximal end portion of the tubular body and defining an inflation port, the inflation lumen providing fluid communication between the inflation port and the second balloon; and a flexible stent mounted on and about said middle balloon.

18. The multi-purpose balloon catheter of claim 17, wherein said at least one proximal perfusion port is located proximally of said proximal balloon and said at least one distal perfusion port is located distal to said third balloon.

19. A multi-purpose balloon catheter, comprising a tubular body having a proximal end portion, a distal end portion, and defining at least two lumens within said tubular body, said distal end portion having three spaced apart balloons thereon, said balloons being positioned proximal, middle, and distal relative to each other, the distal balloon being an occlusive balloon, the middle balloon being a stent mounting balloon and the proximal balloon being an occlusive balloon, wherein said middle balloon has an electrode forming stent mounted thereon, and said tubular body has an electric wire connected to said electrode forming stent which extends through said tubular body to said proximal end portion, wherein said proximal balloon is a drug delivery balloon and has drug delivery outlet ports that open onto an inwardly facing surface of said proximal balloon that faces inwardly toward said tubular body.

20. A multi-purpose balloon catheter, comprising:

a tubular catheter body having a proximal and distal end portion, said tubular body defining a first, second and third inflation lumen;

a first, second and third balloon affixed to said distal end portion of the tubular body and being longitudinally spaced from each other, said first balloon being a relatively elastic occlusive balloon positioned proximal of the second balloon, and the second balloon being a stent mounting balloon positioned proximal of the third balloon, the third balloon being a transparent or translucent photodynamic therapy balloon;

wherein said first, second and third inflation lumen communicate with the first, second and third balloon, respectively; and a light delivery fiber extending within the tubular body to said third balloon to provide light energy to the interior of the third balloon.

21. The multi-purpose balloon catheter of claim 20, further comprising at least one proximal perfusion port located proximally of said proximal balloon and at least one distal perfusion port located distally of said proximal perfusion port being defined by said tubular body, and a perfusion lumen communicating between said proximal and distal perfusion ports.

* * * * *